(12) United States Patent
Robinson et al.

(10) Patent No.: US 11,654,089 B2
(45) Date of Patent: May 23, 2023

(54) NON-WOVEN WATER-SOLUBLE WIPE

(71) Applicant: L'Oreal, Paris (FR)

(72) Inventors: Michael Robinson, Brooklyn, NY (US); Jean-Pascal Hirt, Saint-Cloud (FR); William Bickford, Scotch Plains, NJ (US)

(73) Assignee: L'OREAL, Paris (FR)

( * ) Notice: Subject to any disclaimer, the term of this patent is extended or adjusted under 35 U.S.C. 154(b) by 205 days.

(21) Appl. No.: 16/986,087

(22) Filed: Aug. 5, 2020

(65) Prior Publication Data

US 2021/0038485 A1    Feb. 11, 2021

Related U.S. Application Data

(60) Provisional application No. 62/883,010, filed on Aug. 5, 2019.

(51) Int. Cl.

| | |
|---|---|
| *A61K 8/02* | (2006.01) |
| *A61K 8/81* | (2006.01) |
| *A61Q 1/14* | (2006.01) |
| *C08J 5/18* | (2006.01) |
| *C11D 17/04* | (2006.01) |

(52) U.S. Cl.
CPC ............ *A61K 8/0208* (2013.01); *A61K 8/027* (2013.01); *A61K 8/8129* (2013.01); *A61Q 1/14* (2013.01); *C08J 5/18* (2013.01); *C11D 17/042* (2013.01); *A61K 2800/28* (2013.01); *C08J 2329/04* (2013.01)

(58) Field of Classification Search
None
See application file for complete search history.

(56) References Cited

U.S. PATENT DOCUMENTS

| | | | |
|---|---|---|---|
| 3,881,210 A | 5/1975 | Drach et al. | |
| 6,202,845 B1 | 3/2001 | Hill | |
| 7,465,266 B2 | 12/2008 | Lange et al. | |
| 2007/0098749 A1 | 5/2007 | Eknoian et al. | |
| 2007/0134304 A1* | 6/2007 | Aubrun-Sonneville | A61Q 19/10 424/443 |
| 2008/0013574 A1 | 2/2008 | Aubrun-Sonneville et al. | |
| 2018/0338890 A1 | 11/2018 | Glenn, Jr. et al. | |

FOREIGN PATENT DOCUMENTS

| | | |
|---|---|---|
| EP | 0636716 A1 | 2/1995 |
| EP | 1795172 A1 | 6/2007 |
| EP | 1795173 A1 | 6/2007 |
| JP | H09216809 A | 8/1997 |
| JP | 2007-153900 A | 6/2007 |

(Continued)

OTHER PUBLICATIONS

International Search Report and Written Opinion, dated Nov. 6, 2020, in corresponding International Patent Application No. PCT/US2020/045027, 27 pages.

(Continued)

*Primary Examiner* — Jeffrey D Washville
(74) *Attorney, Agent, or Firm* — Christensen O'Connor Johnson Kindness PLLC

(57) ABSTRACT

Water-soluble cleansing wipes or pads comprising a water-soluble support and their uses in the cosmetic field for cleansing of the skin are disclosed.

15 Claims, 3 Drawing Sheets

(56) References Cited

FOREIGN PATENT DOCUMENTS

| | | |
|---|---|---|
| JP | 2013-136550 A | 7/2013 |
| JP | 2014-152160 A | 8/2014 |
| JP | 2017-114030 A | 6/2017 |
| WO | 2012003349 A2 | 1/2012 |
| WO | 2015097101 A1 | 7/2015 |

OTHER PUBLICATIONS

Japanese Office Action dated Jan. 24, 2023 issued in corresponding Japanese Application Patent No. 2022-502097, (10 pages).
Chinese Office Action dated Mar. 17, 2023, issued in corresponding Chinese Patent Application No. 202080048053X, (14 pages).

* cited by examiner

NON-WOVEN WATER-SOLUBLE WIPE

CROSS-REFERENCE TO RELATED APPLICATION

This application claims the benefit of U.S. Provisional Application No. 62/883,010, filed Aug. 5, 2019; the content of which is hereby incorporated by reference in its entirety.

FIELD OF THE INVENTION

Water-soluble cleansing wipes or pads comprising a water-soluble support and uses thereof in the cosmetic field for cleansing of the skin are disclosed.

BACKGROUND

Currently, cosmetic cleansing non-woven wipes are typically made from cotton or a combination of cotton and polymeric fibers that are spun-woven or needle punched. Such wipes are compostable or disposable by conventional flushing and landfill disposal, respectively. Furthermore, current cosmetic cleansing routines typically require use of liquid products such as cleansers and lotions. These widely used liquid products have disadvantages in terms of packaging, storage, transportation, and convenience of use, and liquid product containers are generally not recyclable.

While water-soluble fibrous cleansing wipes that can be dissolved in the palm of the consumer's hand to reconstitute a liquid product, such as a facial cleanser, have been developed, there are no known solutions that can provide a complete, convenient "bottle-free" facial cleansing routine.

Thus, a need exists for an easily disposable, "bottle-free" cleansing product that combines multiple functionalities, such as a makeup remover and cleanser, and can be produced in an economical manner.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, provided herein is a cleansing pad or wipe comprising one or more non-woven sheets comprising water-soluble fibers, wherein the sheets are soluble in running or standing water having a temperature of 30° C. or less and durable when contacted with an anhydrous formulation comprising 5 wt % of water or less.

In some embodiments, the water-soluble fibers can a water-soluble polymer, for example, comprise polyvinyl alcohols, hydroxy(C1-C6)alkyl celluloses, methylcelluloses, carboxymethylcelluloses, polyvinylpyrrolidones, polyalkylene oxides, gelatins, copolymers of acrylic acid and methacrylic acid, or combinations thereof. In certain embodiments, the water-soluble fibers are polyvinyl alcohol fibers.

In some embodiments, at least one sheet of the one or more sheets is spun-wound non-woven sheet or needle-punched non-woven sheet.

In some embodiments, the water-soluble fibers are functionally modified by mechanical treatment, chemical treatment, or coating. In some embodiments, mechanical treatment is selected from micro-creeping, mechanical bonding, and a combination thereof.

In some embodiments, the fibers are coated with a coating which comprises a hydrophobic composition. In some embodiments, the fibers comprise a hydrophobic coating.

In certain embodiments, the hydrophobic coating comprises silicone, hydrocarbons, natural oils, glycerin, lycopodium powder, water displacement solvent, or a combination thereof.

In some embodiments, the pad further comprises an anhydrous surfactant composition associated with the fibers.

In some embodiments, at least one of the sheets is a makeup removing sheet. In some embodiments, the pad comprises at least one sheet comprising a surfactant composition associated with the fibers. In some embodiments, the pad further comprises at least one exfoliating sheet.

In some embodiments, the pad comprises two or more sheets. In some embodiments, at least two of the two or more sheets are heat sealed.

In some embodiments, the sheets have a thickness of about 0.3 mm to about 0.5 mm. In certain embodiments, the pad further comprises a barrier film between two adjacent sheets. In some embodiments, the film is water soluble. In some embodiments, the film comprises polyvinyl alcohol. In some embodiments, the pad further comprises a cleansing pod positioned between two adjacent sheets, wherein the cleansing pod comprises a powdered surfactant composition encapsulated in a water-soluble nonwoven pad or water soluble film. In some embodiments, the two or more sheets are detachable.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Disclosed herein are sustainable cleansing products such as wipes or pads comprising at least one sheet containing water-soluble fibers. Each pad combines at least two functionalities, such as a makeup and dirt removal, exfoliation of skin cells, and skin cleansing.

In one aspect, provided herein is a cleansing pad comprising one or more non-woven sheets comprising water-soluble fibers, wherein the sheets are soluble in running or standing water having a temperature of 30° C. or lower and durable when contacted with an anhydrous formulation comprising 5 wt % of water or less.

Figure 1A:
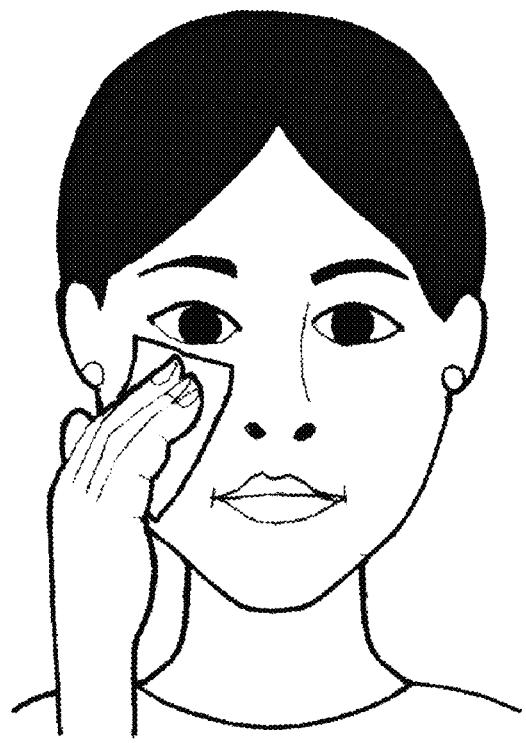
FIGS. 1A-1D demonstrate the facial cleansing routine using an exemplary pad: use makeup removing sheet to remove makeup, e.g., with oil-based solution and discard (FIG. 1A), wet cleansing sheet with water, by rinsing it lightly under water (FIG. 1B), use water-rinsed sheet on face (FIG. 1C), the sheet completely dissolves into a foamy cleanser that the user can use as a second step after removal of makeup (FIG. 1D).
Figure 1B:
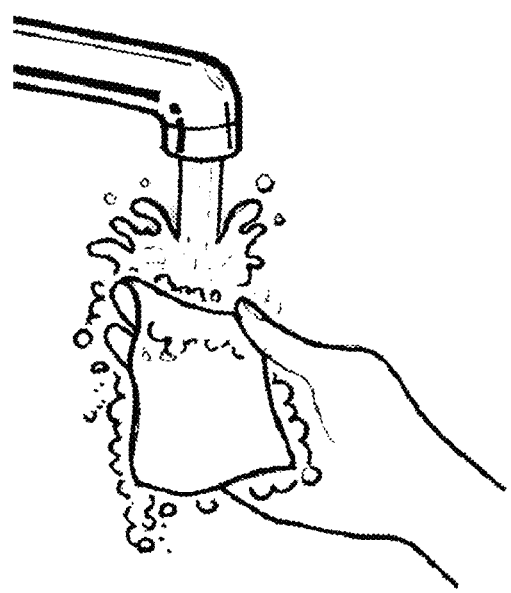
Figure 1C:
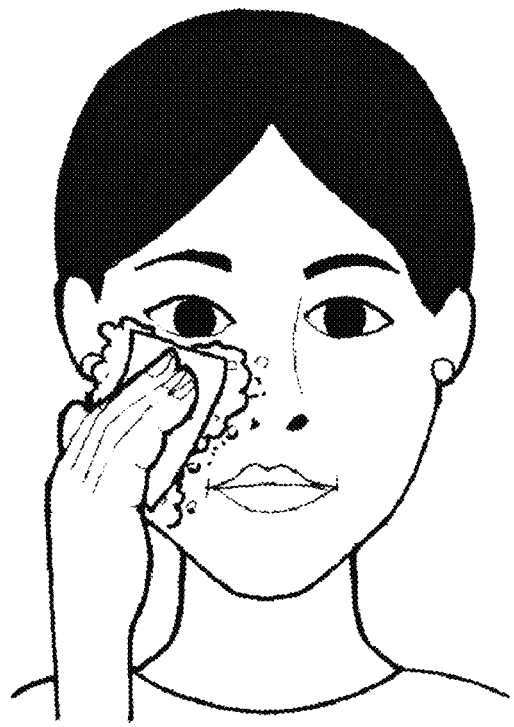
Figure 1D:
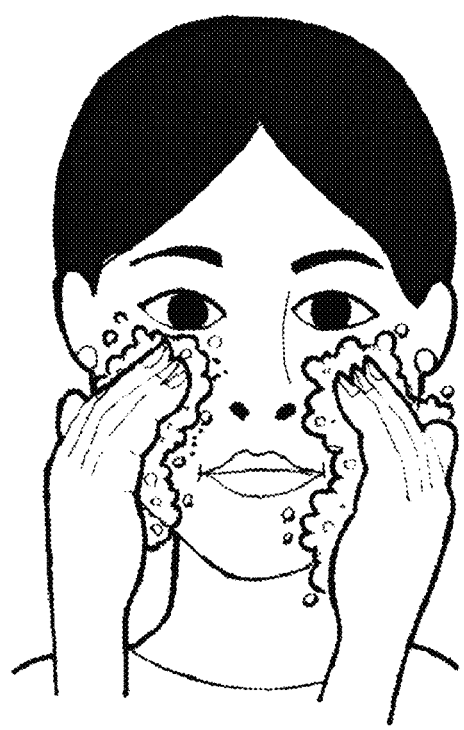

Throughout the disclosure, the terms "wipe" and "pad" are used interchangeably. The pads disclosed herein can provide the user with a complete product for facial cleansing routine that includes all necessary components such as makeup remover and cleanser and does not require the use of additional liquid components. For example, in one embodiment, the pad comprises at least one sheet that can be used as a makeup removal sheet, e.g., a non-woven sheet comprising fibers that have a texture. This sheet can also incorporate an anhydrous surfactant component associated with the pad as described below. After using the pad to remove makeup and/or oils and dirt from the surface of the skin (e.g., face), the pad can be quickly dissolved in the palm of the consumer's hand to reconstitute a liquid surfactant product that can be used to wash the skin, thus completing the routine. Alternatively, a user can use one of such dual-function pads to remove makeup and dispose it by flushing or dissolving under running water and use a second pad to cleanse the skin by reconstituting the anhydrous surfactant component into a liquid cleanser, for example, as shown in FIGS. 1A-1D.

In another embodiment, the pad comprises two or more layers or sheets that have distinct functions and/or are distinctly functionalized, as described below. For example, in one embodiment, the pad comprises one or more makeup removal sheets and at least one cleansing sheet comprising a surfactant composition, for example, dry surfactant composition, associated with the sheet. In certain embodiments, the pad further comprises one or more exfoliating sheets. The sheets can be arranged in any manner. Typically, one or more makeup removing sheets are positioned on the top of one or more cleansing and/or exfoliating sheets. The user can detach a makeup removing sheet from the pad and use the sheet to wipe the skin to remove makeup and/or dirt. The used sheet can then be discarded by flushing or dissolving under running water. Following the makeup removal, the user can reconstitute the remaining sheet or sheets in water to provide a surfactant cleanser and use the cleanser to wash the skin. Yet in further embodiments, the pad can comprise two or more sheets sealed together at the edges and a cleansing pod inserted between two adjacent sheets, wherein the cleansing pod comprises a powdered surfactant composition encapsulated in a water-soluble non-woven pad or water-soluble film. Typically, when the pad comprises two or more sheets, the two or more sheets are detachable.

The pad disclosed herein can have any shape, e.g., a shape appropriate to the intended use, such as for removal of makeup around the eye. For example, the pad can have a rectangular, round, kidney, or oval shape that has dimensions suitable for the intended use. Thus, the pad can be of oval shape about 2 cm to 15 cm long and about 1 cm to 10 cm wide, or of disc shape with a diameter of about 2 cm to 15 cm, or in the form of a square with sides of about 5 cm to 15 cm, or in the form of a rectangle about 5 cm to 15 cm long.

The pads are preferably completely soluble in tap water of a temperature suitable for facial cleansing, for example, a temperature of 30° C. or lower. As used herein, "30° C. or lower" means a temperature that does not exceed 30° C. but is not less than 0° C., such as a temperature of from about 0° C. to about 30° C., or for example, ranging from more than about 0° C. to about 30° C., from about 5° C. to about 30° C., from about 10° C. to about 30° C., from about 15° C. to about 30° C., or from about 20° C. to about 30° C. In certain embodiments, the entire pad is soluble in water at a temperature of 30° C. or lower. As used herein, the term "water-soluble" is used to describe a material or an object that substantially or completely dissolves in water of the temperatures described above. In some embodiments, the complete dissolution occurs within about 0.5 minutes to about 30 minutes, within about 1 minute, within about 3 minutes, within about 5 minutes, or within about 10 minutes.

The pads or wipes disclosed herein comprise sheets that are substantially free of water-insoluble fibers. In some embodiments, the pad includes sheets that consist of fibers that are water-soluble, so that the entire pad is completely water-soluble. According to one embodiment, the sheets do not have any water-insoluble fibers, i.e., the sheets are composed solely of water-soluble fibers, so that the entire sheet is completely soluble in water.

Any suitable water-soluble fibers can be used in the manufacturing of the pads disclosed herein, such as natural, artificial, or synthetic water-soluble polymeric fibers. In some embodiments, the water-soluble fibers comprise water-soluble polymeric material. Any water-soluble material that can be spun into fibers can be used in the preparation of the sheets of the pads disclosed herein, such as materials selected from polyvinyl alcohols, hydroxy(C1-C6)alkyl celluloses, methylcelluloses, carboxymethylcelluloses, polyvinylpyrrolidones, polyalkylene oxides, gelatins, copolymers of acrylic acid and methacrylic acid, and combinations thereof.

In certain embodiments, the water-soluble fibers are polyvinyl alcohol (PVA) fibers that are made with polyvinyl alcohol (PVA) by a method that provides the required water solubility of the fiber. The PVA used in the fibers can have various degrees of polymerization. For instance, PVA fibers that are soluble in water at a temperature less than or equal to 30° C. include PVA fibers that are marketed by the Japanese company Kuaray under the trade name Kuralon K-II™ WN2. The fibers comprises are prepared by a method that includes preparation of a spinning solution by dissolving a water-soluble PVA-based polymer in a first organic solvent, spinning of the solution in a second organic solvent to obtain solidified threads, and wet drawing of the threads from which the first solvent is removed and which are then dried and undergo a heat treatment. These fibers can have a circular cross-section and have a tensile strength of at least 2.7 g/dtex (3 g/d), as described in European Patent Application EP0636716, the disclosure of which is incorporated herein by reference in its entirety. Other types fibers in addition or in the place of PVA can be used in the sheets of the pads disclosed herein, such as but not limited to polysaccharide fibers marketed under the name Lysornb® by Lysac Technologies, or polyholoside polymer-based fibers such as glucomannan or starch. When a combination of fibers is used in the pads disclosed herein, where appropriate, the fibers can comprise a mixture of various fibers that are water-soluble at different temperatures, such as different temperatures of 30° C. or lower. In some embodiments, each sheet of the one or more sheets comprises two or more types of water-soluble fibers. In other embodiments, the pads can comprise two or more sheets wherein at least two sheets comprise a different type of water-soluble material.

The pads disclosed herein comprise one or more sheets of fibers. The terms "sheet" and "layer" are used interchangeably throughout the disclosure. As used herein, a non-woven sheet is a sheet which is different from a thin film.

The pads disclosed herein comprise at least one non-woven sheet. In some embodiments, the non-woven sheet is a spun-wound sheet or a needle-punched sheet. Any suitable techniques for making a nonwoven material from fibers can be used in the manufacturing of the pads disclosed herein. For example, the fibers can be formed by extrusion and deposited on a conveyor to form a sheet of fibers which is then consolidated by a conventional fiber bonding technique, for example needling, hot bonding, or calendaring. In some embodiments, bonding by jets of hot air (i.e., air through bonding), a technique in which the sheet passes through a tunnel into which hot air is blown, can be employed, preferably when the sheet is composed of fibers comprising two types of material. Fibers suitable for this method include fibers comprising at least two grades of polyvinyl alcohol (PVA) of different melting points or softening points. These fibers can be co-extruded in such a way that the fiber has PVA of at least one first grade located in the core of the fiber and PVA of at least one second grade located at the periphery of the fiber, e.g., forming a sheath around the core. Bonding of such core-sheath fibers can be easier achieved when the sheath has a lower melting point than the core.

Figure 2A:
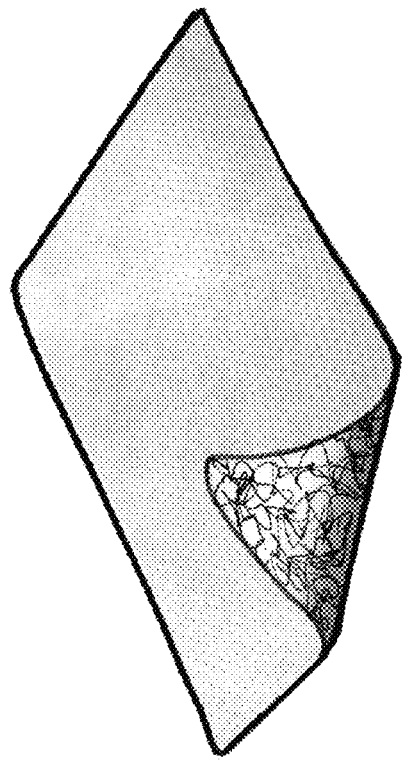
FIGS. 2A-2D show exemplary pads: regular nonwoven single sheet pad (FIG. 2A), pad with heat-sealed edges (FIG. 2B), layered pad with heat-sealed edges (FIG. 2C), and layered pad with an oil-soaked PVA (makeup removing) sheet on one side, PVA cleansing sheet on the other side, and an embedded PVA film on the inside (FIG. 2D).
Figure 2B:
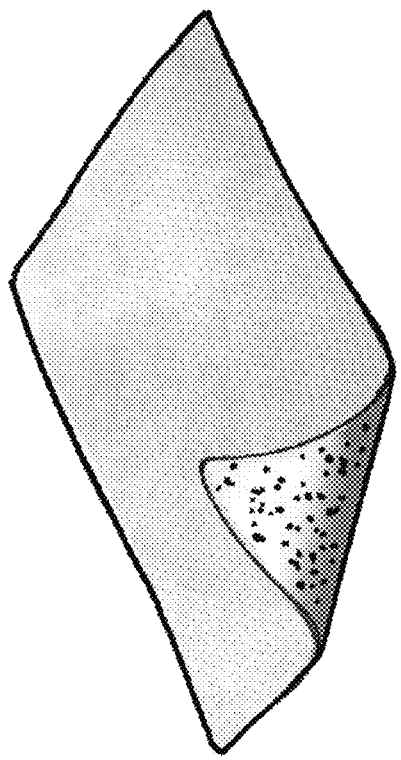
Figure 2C:
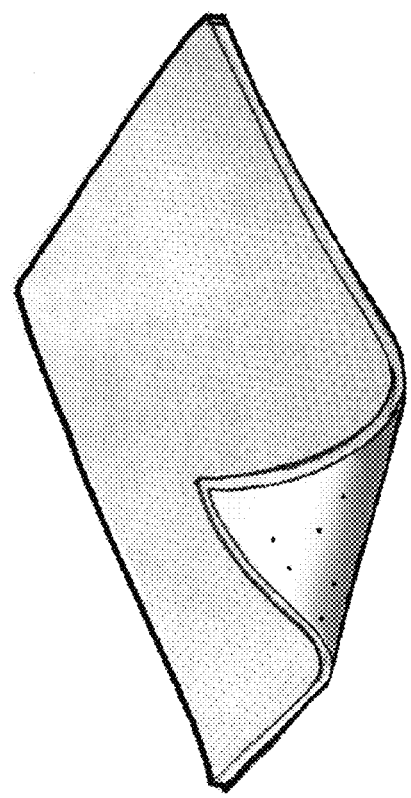
Figure 2D:
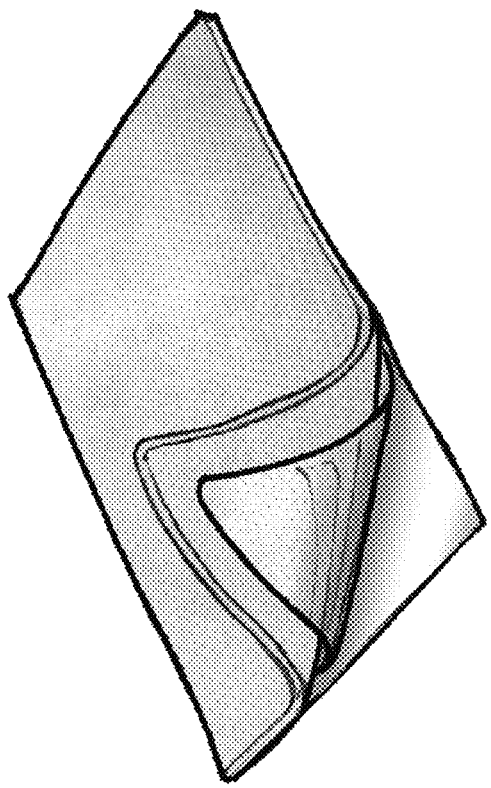
Figure 3:
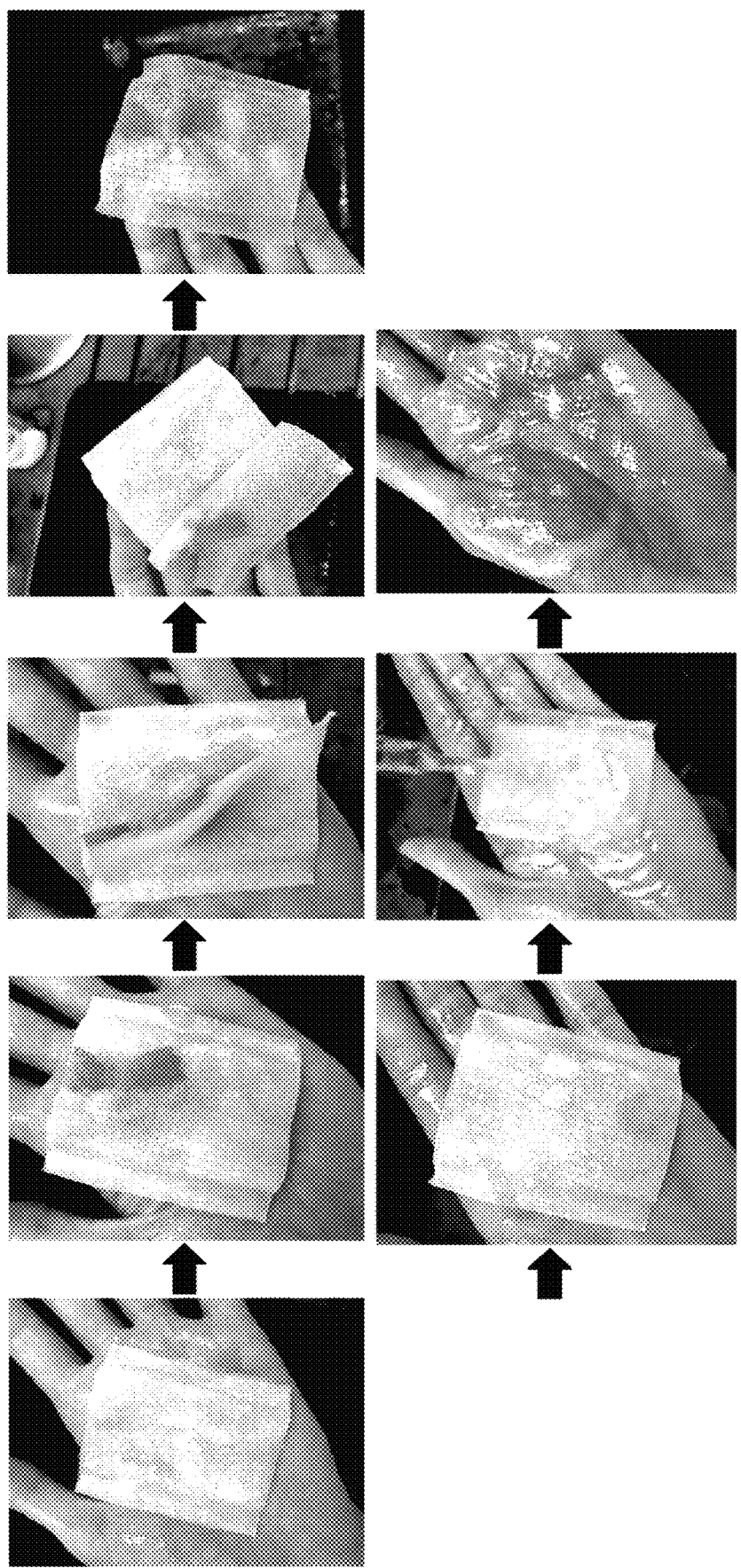
FIG. 3 are photographs of makeup removal and cleansing steps using an exemplary wipe.

When the pads disclosed herein comprise several sheets, two or more sheets can be joined together in a variety of ways, for example by welding, gluing, or stitching, for instance, by stitching with a thread that is itself water-soluble. In some embodiments, when the pad comprises several non-woven sheets, these sheets can be joined together by heat sealing, for example, by heat sealing the edges of the pads or on their periphery so as to provide a pad with an internal cavity. In some embodiments, when the pad comprises two or more layered sheets, at least a portion of the edge of the pad is heat-sealed creating a "living hinge" that allows for ease of folding and shaping the non-woven material for packaging and consumer use. In some embodiments, the pad or one or more sheets of the pad can be textured, for example, by subjecting to pressure and/or heat to form texture. Exemplary pads are shown in FIGS. 2A-2D.

In some embodiments, the pad can comprise an edge portion and a central portion surrounded by the edge portion wherein the edge and the central portions have different dissolution times. In one embodiment, the pad comprises a non-woven PVA central portion comprising a hydrophobic coating and optionally anhydrous surfactant composition associated with the coating, and a PVA edge portion that does not have a coating. In some embodiments, the edge portion has a faster dissolution time than the central portion when contacted with water at a temperature of 30° C. or lower. In some embodiments, the shape of the pad, when combining with hydrophobic coated areas and heat sealed areas, can be tailored to a specific utility, for example, a kidney-shaped pad for cleansing the corner of the eye.

In some embodiments of the pads or wipes disclosed herein, the surface of the water-soluble fibers is functionally modified or functionalized by a suitable treatment such as mechanical treatment, chemical treatment, coating, or a combination thereof. Functionalization by mechanical and/or coating and/or chemical means is used to provide a specific property, such as but not limited to cleansing, absorption, skin exfoliation, containment of active ingredients, deposition of active ingredients, durability, or a combination thereof.

In some embodiments, the fibers are mechanically modified. Mechanical treatment, such as treatment selected from micro-creeping (calendar pressure and heat), mechanical bonding, and a combination thereof, can be used to increase sheet volume, create physical texture, or alter absorption characteristics (e.g., provide more volume or higher absorption rate). In certain embodiments, mechanical bonding, such as heat forming and/or sealing, can create physical textures and alter absorption and dissolution characteristics (i.e., bonds increase dissolution time, reduce absorption rates, and create rough areas or durable areas), or can be used to create pointed, linear, linear patterns, or co-planar seals.

In certain embodiments, the fibers comprise a coating. In some embodiments, the coating is a hydrophobic coating. Coating the fibers of the pads disclosed herein can be achieved in any suitable manner by contacting the individual water-soluble fibers or a sheet comprising the fibers with a hydrophobic composition, e.g., a coating can be calendared, sprayed on, fused to, or soaked/saturated within/on the non-woven sheets such as PVA non-woven sheets. Hydrophobic coatings can inhibit solubility with water and/or provide a barrier on one or both sides of the non-woven sheet. Additionally, film coating can function as a barrier to or between one or more non-woven sheets (e.g., PVA sheets) impregnated with incompatible formulas that need to deliver a distinct benefit or effect, e.g. separating PVA sheet soaked in oil for makeup removal from a PVA sheet impregnated with a powder surfactant composition for cleansing and "sudsing" effect, which serves a major efficacy cue for the users, upon contact with water.

The pads or wipes disclosed herein can be used with any suitable makeup removing formulations. For example, an exemplary pad can comprise one or more makeup removal sheets having fibers coated with makeup removal formulation such as an oil. Examples of makeup removing formulations are known in the art. For instance, in some embodiments, the pad comprises a makeup removing composition of Table 1.

TABLE 1

Exemplary makeup removal compositions

| Name | Composition 1 | Composition 2 | Composition 3 |
|---|---|---|---|
| Water (QS) | 66.95 | 68.25 | 68.4 |
| Acrylates/C10-C30 alkyl acrylate crosspolymer | 0.05 | 0.05 | 0.05 |
| Glycerin | 5 | 5 | 5 |
| Hydroxyacetophenone | 0.5 | 0.5 | 0.5 |
| Pentyleneglycol | 1.5 | | |
| Piroctone Olamine | | 0.2 | 0.05 |
| Isohexadecane | 10 | 10 | 10 |
| Isopropyl Myristate | 10 | 10 | 10 |
| Dimethicone | 3.5 | 3.5 | 3.5 |
| Sodium Acrylates Copolymer (and) Caprylic/Capric Triglyceride | 2.5 | 2.5 | 2.5 |
| Total (%): | 100 | 100 | 100 |

In some embodiments, the fibers comprising the sheets comprise a hydrophobic coating. Suitable hydrophobic coatings include coatings comprising silicone, hydrocarbons, natural oils, glycerin, lycopodium powder, water displacement solvents, or combinations thereof. The coating can further serve as an adhesive for additional functionality, such as powdered detergent or surfactant composition or an exfoliating composition. Surfactants and exfoliating agents are known in the art.

In some embodiments, the pads disclosed herein comprise a makeup removing sheet which is a textured PVA sheet or a PVA sheet that has a makeup removing agent such as a cleansing oil associated with it. In some embodiments, the pads further comprise an anhydrous surfactant composition associated with the fibers, as described above. Suitable surfactant compositions can comprise SLS, fats, alkalis, essential oils, fragrances, glycerin, blends, cocoa butter. The surfactants can be dry surfactants, such as powdered surfactants or present in other anhydrous forms, e.g., having less than about 5%, less than about 3%, or less than about 1% by weight water. Yet in further embodiments, in addition to the sheets described herein, the pad further comprises at least one exfoliating sheet, e.g., a sheet having an exfoliating agent associated with the sheet. Thus, in some embodiments, the pad comprises multiple sheets, e.g., two or more sheets, three or more sheets, four or more sheets, or five or more sheets. In some embodiments, the pad comprises two sheets, three sheets, four sheets, five sheets, six sheets, seven sheets, eight sheets, nine sheets, or ten sheets. In some embodiments, when the pad comprises two or more sheets, the at least two of the two or more sheets are heat sealed. In some embodiments, the sheets can comprise incompatible formulae or have different functionalities. The pad disclosed herein can further comprise a barrier film between any two adjacent sheets, for example, sheets that have incompatible functionalities or formulae. The film is composed of a water soluble material, for example, in some embodiments, the film comprises polyvinyl alcohol. PVA films are known in the art and are offered commercially by a number of manufacturers.

Any thickness sheets can be used in the pads disclosed herein. In certain embodiments, the sheets have a thickness of from about 0.30 mm to about 0.50 mm, about 0.30 mm to about 0.60 mm, or about 0.30 mm to about 1.0 mm. In some embodiments, the sheets have a thickness of about 0.40 mm to about 0.45 mm.

The pads disclosed herein can be manufactured by methods known in the art, for example, the processes disclosed in U.S. Pat. Nos. 7,465,266 and 6,202,845 which are incorporated herein in their entirety. For example, a multi-layered, non-woven exemplary PVA pad can be manufactured by fusing one or more non-woven PVA sheets with PVA film to create a multi-layered pad that separates incompatible formulae. In an embodiment, three webs or sheets of material, e.g., a makeup removing non-woven PVA fiber sheet, a PVA film, and a cleansing PVA sheet having the characteristics described above, are bought together, in an in-line manufacturing process, using a sealing (layer to layer) step and cutting/scoring step to allow for "z-folding", and alternate "z-folding" that allows for compatible formulas on alternating sides of the pad to be in contact, avoiding two incompatible formulas from touching each other. The method is useful to separate substrates that are impregnated and/or coated with formulae to avoid reaction (e.g., oil/surfactant foam neutralization) during manufacturing and packaging of multi-layer non-woven pads, and throughout consumer use (i.e., the pads dispense in a reverse "z-fold").

In an additional aspect, provided herein is a kit or a package comprising at least one pad as disclosed herein. In some embodiments, the kit comprises multiple pads. In certain embodiments, the pads are removably attached to each other and/or folded into a reverse z-fold as described above.

Unless otherwise indicated, all numbers expressing quantities or conditions are to be understood as being modified in all instances by the term "about," meaning within 10% of the indicated number (e.g. "about 10%" means 9%-11% and "about 2%" means 1.8%-2.2%). All percentages and ratios are calculated by weight unless otherwise indicated. All percentages are calculated based on the total composition unless otherwise indicated. Unless otherwise expressly stated, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All publications and patent applications cited in this specification are herein incorporated by reference, and for any and all purposes, as if each individual publication or patent application were specifically and individually indicated to be incorporated by reference.

While illustrative embodiments have been illustrated and described, it will be appreciated that various changes can be made therein without departing from the spirit and scope of the invention.

The embodiments of the invention in which an exclusive property or privilege is claimed are defined as follows:

1. A cleansing pad comprising two or more non-woven sheets comprising water-soluble fibers, wherein the sheets are soluble in running or standing water having a temperature of 30° C. or less and durable when contacted with an anhydrous formulation comprising 5 wt % of water or less, at least a first sheet is soaked in makeup removal oil and at least a second sheet includes an anhydrous surfactant, wherein the first sheet is separable from the second sheet, each sheet is designated to perform a different function.

2. The pad of claim 1, wherein the water-soluble fibers comprise materials selected from the group consisting of polyvinyl alcohols, hydroxy(C1-C6)alkyl celluloses, methylcelluloses, carboxymethyl celluloses, polyvinylpyrrolidones, polyalkylene oxides, gelatins, copolymers of acrylic acid and methacrylic acid, and combinations thereof.

3. The pad of claim 1, wherein at least one sheet is spun-wound non-woven sheet or needle-punched non-woven sheet.

4. The pad of claim 1, wherein the water-soluble fibers are polyvinyl alcohol fibers.

5. The pad of claim 4, wherein the surface of the water-soluble fibers is functionally modified by mechanical treatment, chemical treatment, or coating.

6. The pad of claim 5, wherein the mechanical treatment is selected from the group consisting of micro-creeping, mechanical bonding, and a combination thereof.

7. The pad of claim 5, wherein the coating comprises a hydrophobic composition.

8. The pad of claim 1, wherein the water-soluble fibers comprise a hydrophobic coating.

9. The pad of claim 8, wherein hydrophobic coating comprises materials selected from the group consisting of silicone, hydrocarbons, natural oils, glycerin, lycopodium powder, water displacement solvent, and combinations thereof.

10. The pad of claim 8, wherein the pad further comprises an anhydrous surfactant composition associated with the fibers.

11. The pad of claim 1, wherein the sheets have a thickness of about 0.3 mm to about 0.5 mm.

12. The pad of claim 1, wherein the pad further comprises a barrier film between the first and second sheets.

13. The pad of claim 12, wherein the film is water-soluble.

14. The pad of claim 12, wherein the film comprises polyvinyl alcohol.

15. The pad of claim 11, wherein the pad further comprises a cleansing pod between two adjacent sheets, wherein the cleansing pod comprises a powdered surfactant composition encapsulated in a water-soluble nonwoven pad or a water-soluble film.

* * * * *